US012657868B2

(12) United States Patent
Kim et al.

(10) Patent No.: US 12,657,868 B2
(45) Date of Patent: Jun. 16, 2026

(54) DENTAL TREATMENT DATA MATCHING METHOD AND DIGITAL DENTISTRY DEVICE THEREFOR

(71) Applicant: OSSTEM IMPLANT CO., LTD., Seoul (KR)

(72) Inventors: Hwa Sam Kim, Gimpo-si (KR); Kyoo Ok Choi, Seoul (KR)

(73) Assignee: OSSTEM IMPLANT CO., LTD., Seoul (KR)

( * ) Notice: Subject to any disclaimer, the term of this patent is extended or adjusted under 35 U.S.C. 154(b) by 278 days.

(21) Appl. No.: 18/565,829

(22) PCT Filed: May 12, 2022

(86) PCT No.: PCT/KR2022/006805
§ 371 (c)(1),
(2) Date: Nov. 30, 2023

(87) PCT Pub. No.: WO2023/286994
PCT Pub. Date: Jan. 19, 2023

(65) Prior Publication Data
US 2024/0265670 A1 Aug. 8, 2024

(30) Foreign Application Priority Data
Jul. 13, 2021 (KR) ........................ 10-2021-0091654

(51) Int. Cl.
*G06V 10/75* (2022.01)
*G06V 10/26* (2022.01)
(Continued)

(52) U.S. Cl.
CPC .............. *G06V 10/75* (2022.01); *G06V 10/26* (2022.01); *G06V 10/457* (2022.01); *G16H 20/40* (2018.01); *G06V 2201/03* (2022.01)

(58) Field of Classification Search
CPC ...... G06V 10/75; G06V 10/457; G06V 10/26; G06V 2201/03; G16H 20/40
See application file for complete search history.

(56) References Cited

U.S. PATENT DOCUMENTS 9,424,461 B1 * 8/2016 Yuan .................... G06V 20/647
10,483,004 B2 * 11/2019 Wu .................... A61C 13/0004
(Continued)

FOREIGN PATENT DOCUMENTS

KR 10-0583183 B1 5/2006
KR 10-2008-0048562 A 6/2008
(Continued)

OTHER PUBLICATIONS

Office action issued on Oct. 25, 2023 in counterpart Korean Patent Application No. 10-2021-0091654 (4 pages Korean).
(Continued)

*Primary Examiner* — John W Miller
(74) *Attorney, Agent, or Firm* — NSIP Law

(57) ABSTRACT

Disclosed are a dental treatment data matching method and a digital dentistry device therefor. In the dental treatment data matching method according to an embodiment, feature points of individual teeth are extracted when carrying out matching between pieces of dental treatment data required for dental treatment plan validation, matching reference points are extracted from among the extracted feature points, and matching between pieces of data is carried out by using the extracted matching reference points, and thus, the accuracy may be increased by improving matching errors, and convenience of use may be increased by minimizing user intervention.

10 Claims, 8 Drawing Sheets

(51) Int. Cl.
    *G06V 10/44*     (2022.01)
    *G16H 20/40*     (2018.01)

(56)            References Cited

U.S. PATENT DOCUMENTS

| | | | |
|---|---|---|---|
| 11,158,121 B1 * | 10/2021 | Tung | G06N 3/0442 |
| 11,259,874 B1 * | 3/2022 | Landon | G16H 40/67 |
| 11,612,454 B2 * | 3/2023 | Kuo | G16H 50/50 |
| | | | 703/6 |
| 2005/0048432 A1 * | 3/2005 | Choi | A61C 7/002 |
| | | | 433/24 |
| 2007/0168152 A1 | 7/2007 | Matov et al. | |
| 2008/0124681 A1 * | 5/2008 | Cha | A61C 9/0053 |
| | | | 703/7 |
| 2011/0044521 A1 * | 2/2011 | Tewfik | G06T 7/251 |
| | | | 382/131 |
| 2018/0168780 A1 | 6/2018 | Kopelman et al. | |
| 2018/0168781 A1 * | 6/2018 | Kopelman | G06T 17/00 |
| 2019/0192258 A1 | 6/2019 | Kang et al. | |
| 2020/0237486 A1 | 7/2020 | Kopelman et al. | |
| 2021/0121271 A1 | 4/2021 | Kopelman et al. | |
| 2021/0298878 A1 | 9/2021 | Kopelman et al. | |
| 2022/0246270 A1 * | 8/2022 | Alvarez | A61C 13/34 |
| 2022/0351829 A1 * | 11/2022 | Xia | G16H 20/40 |
| 2023/0141733 A1 | 5/2023 | Kopelman et al. | |
| 2025/0090284 A1 | 3/2025 | Kopelman et al. | |

FOREIGN PATENT DOCUMENTS

| | | |
|---|---|---|
| KR | 10-2008-0089698 A | 10/2008 |
| KR | 10-1218390 B1 | 1/2013 |
| KR | 10-1930062 B1 | 3/2019 |
| KR | 10-2227460 B1 | 3/2021 |
| KR | 10-2269030 B1 | 6/2021 |
| WO | WO 2018/112273 A2 | 6/2018 |

OTHER PUBLICATIONS

Office action issued on May 18, 2023 in counterpart Korean Patent Application No. 10- 2021-0091654 (9 pages Korean).
Extended European Search Report Issued on May 23, 2025, in Counterpart European Patent Application No. 22842257.2 (11 Pages in English).

\* cited by examiner

REFERENCE DATA          COMPARATIVE DATA

1

DENTAL TREATMENT DATA MATCHING METHOD AND DIGITAL DENTISTRY DEVICE THEREFOR

CROSS REFERENCE TO RELATED APPLICATIONS

This application is a U.S. National Stage Application of International Application No. PCT/KR2022/006805, filed on May 12, 2022, which claims the benefit under 35 USC 119 (a) and 365(b) of Korean Patent Application No. 10-2021-0091654, filed on Jul. 13, 2021, in the Korean Intellectual Property Office, the entire disclosure of which is incorporated herein by reference for all purposes.

TECHNICAL FIELD

The present invention relates to digital dentistry technology, and more specifically, to digital data matching technology.

BACKGROUND ART

When establishing an orthodontic treatment plan, it is possible to create a more stable plan by predicting improved tooth setup from the current state of teeth. In a digital environment, dental models may be freely manipulated in three dimensions, allowing for various plans to be established.

For long-term orthodontic treatment, a process is necessary to verify whether tooth movement has occurred as planned during or after the treatment by monitoring the treatment process and its outcomes. To monitor the treatment process and its outcomes, at least two dental treatment data sets are matched, and the matched data set may be used for the validation of the orthodontic treatment plan. However, depending on the user's experience and knowledge, errors may occur in matching dental treatment data sets due to differences in user experience and knowledge.

DISCLOSURE

Technical Problem

One embodiment of the present invention proposes a dental treatment data matching method capable of improving matching errors occurring when carrying out matching between two pieces of dental treatment data required for validation of a dental treatment plan, as well as reducing the matching processing time, and a digital dentistry device therefor.

Technical Solution

A dental treatment data matching method according to an embodiment includes acquiring at least two pieces of dental treatment data to be matched, separating individual teeth and gum in each of the acquired data, extracting feature points of the individual teeth for each of the separated data, extracting matching reference points based on tooth movement from among the extracted feature points, performing matching between the pieces of data using the extracted matching reference points, and displaying a matching result.

In the extracting of the feature points of the individual teeth, at least one of occlusal-direction feature points or adjacent-direction feature points may be extracted for each of the individual teeth.

The extracting of the matching reference points may include dividing a tooth area into a plurality of regions in each data, determining whether a fixed tooth exists in each divided region by checking tooth movement information of the individual teeth in each divided region, and if there is at least one fixed region where a fixed tooth exists, extracting the matching reference points centered around the fixed tooth, or if all teeth move without a fixed tooth, extracting the matching reference points centered around a tooth with the least tooth movement.

In the extracting of the matching reference points centered around the fixed tooth, if there is at least one fixed region where a fixed tooth exists, three or more feature points that form the largest area when connected may be extracted from among feature points of the fixed tooth as the matching reference points.

In the extracting of the matching reference points centered around the fixed tooth, if there is not at least one fixed region where a fixed tooth exists, a predetermined number of individual teeth with the least tooth movement may be extracted, followed by extracting three or more feature points that form the largest area when connected from among feature points of the extracted individual teeth as the matching reference points.

The dental treatment data matching method may further include, before matching, forming figures by connecting the matching reference points extracted for each data and pre-calculating a deviation between the figures by comparing at least one of the area, position, or size of the formed figures of each data, and the performing of matching between the pieces of data may include, when the calculated deviation between the figures is within a predetermined value range, performing matching between the pieces of data using the extracted matching reference points, or when the calculated deviation between the figures is outside the predetermined value range, modifying the extracted matching reference points, followed by performing matching between the pieces of data using the modified matching reference points.

The dental treatment data matching method may further include at least one of displaying the deviation between the figures of each data as a numerical value on a screen, or displaying the numerical deviation in a distinguished manner using identifiable visual information on the screen.

The dental treatment data matching method may further include providing a user interface for modifying the extracted matching reference points and modifying at least one of the matching reference points by user interaction with the user interface.

In the providing of the user interface, while keeping matching reference points of comparative data fixed, reference matching points of reference data may be reflected and displayed onto the comparative data, and the user interface for modifying the matching reference points of the reference data displayed on the comparative data may also be displayed on a screen.

In the extracting of the feature points of individual teeth for each of the separated data and the extracting of the matching reference points from among the extracted feature points, artificial intelligence-based machine learning on training data including previously accumulated multiple dental treatment data may be performed, and feature points and matching reference points may be extracted from newly input dental treatment data using the training data.

In the displaying of the matching result, after performing data matching, a tooth movement deviation or matching deviation between the data may be displayed in a distinguished manner using identifiable visual information.

A digital dentistry device according to another embodiment includes a data acquisition unit configured to acquire at least two pieces of dental treatment data to be matched, a control unit configured to separate individual teeth and gum in each of the acquired data, extract feature points of the individual teeth for each of the separated data, extract matching reference points based on tooth movement from among the extracted feature points, and perform matching between the pieces of data using the extracted matching reference points, and an output unit configured to display a screen according to an operation of the control unit and display a matching result.

The control unit may divide a tooth area into a plurality of regions in each data, determine whether a fixed tooth exists in each divided region by checking tooth movement information of the individual teeth in each divided region, and if there is at least one fixed region where the fixed tooth exists, extract the matching reference points centered around the fixed tooth, or if all teeth move without a fixed tooth, extract the matching reference points centered around a tooth with the least tooth movement.

The control unit may, before matching, form figures by connecting the matching reference points extracted for each data, pre-calculate a deviation between the figures by comparing at least one of the area, position, or size of the formed figures of each data, and, when the calculated deviation between the figures is within a predetermined value range, perform matching between the pieces of data using the extracted matching reference points, or when the calculated deviation between the figures is outside the predetermined value range, modify the extracted matching reference points, followed by performing matching between the pieces of data using the modified matching reference points.

The control unit may display a user interface for modifying the extracted matching reference points on a screen through the output unit and modify at least one of the matching reference points by user interaction with the user interface.

A dental treatment data matching method which is supported by one or more processors may include obtaining a plurality of feature points associated with individual teeth from at least two pieces of scan data, determining at least three of the plurality of feature points as matching reference points based on the areas of figures formed by using at least some of the plurality of feature points as vertices, and performing matching between the at least two pieces of scan data using the at least three matching reference points.

A dental treatment data matching method which is supported by one or more processors may include obtaining at least two pieces of scan data that can be divided into a first region corresponding to anterior teeth, a second region corresponding to left posterior teeth, and a third region corresponding to right posterior teeth, designating each of the first to third region as either a fixed region or a moving region based on tooth movement information, determining three or more matching reference points in at least one of the first to third regions by applying different conditions based on the number of fixed regions, and performing matching between the at least two pieces of scan data using the determined matching reference points.

Advantageous Effects

According to a dental treatment data matching method and a digital dentistry device therefor in accordance with an embodiment, when carrying out matching between pieces of dental treatment data required for dental treatment plan validation, the accuracy may be increased by improving matching errors, and convenience of use may be increased by minimizing user intervention.

For example, by automatically providing a matching result with the input of at least two pieces of dental treatment data, user manipulation may be minimized. Additionally, the device initially provides a comparison of matching reference points before matching, allowing the user to confirm the comparison result, and thus, manual user intervention for monitoring the process and outcomes of orthodontic treatment after creating a treatment plan may be minimized and treatment plan creation time may be reduced.

The precise extraction of matching reference points based on tooth movement and utilizing these extracted matching reference points for data matching between pieces of dental treatment data contributes to improved matching errors during matching. Errors and variations in treatment planning may be reduced, compared to conventional methods that rely on user knowledge, leading to the establishment of high-quality treatment plans.

DESCRIPTION OF DRAWINGS

FIG. 4 illustrates screens for extracting matching reference points for matching between pieces of data according to an embodiment of the present invention.

FIG. 5 illustrates screens for matching between pieces of data using matching reference points extracted according to an embodiment of the present invention.

MODE OF THE INVENTION

Figure 1:
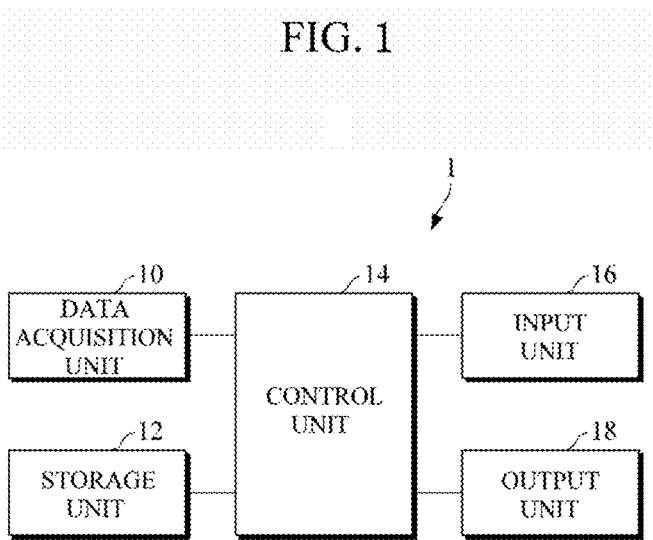
FIG. 1 a diagram illustrating the configuration of a digital dentistry device according to an embodiment of the present invention.

The advantages and features of the present invention and the manner of achieving the advantages and features will become apparent with reference to embodiments described in detail below together with the accompanying drawings. However, the present invention may be implemented in many different forms and should not be construed as being limited to the embodiments set forth herein, and the embodiments are provided such that this disclosure will be thorough and complete and will fully convey the scope of the present invention to those skilled in the art, and the present invention is defined only by the scope of the appended claims. Throughout the entire specification, the same or like reference numerals designate the same or like elements.

In describing the example embodiments, a detailed description of related known configurations or functions incorporated herein will be omitted when it is determined that the detailed description thereof may unnecessarily obscure the subject matter of the present invention. The terms which will be described below are terms defined in consideration of the functions in the present invention, and may be different according to users, intentions of the users, or customs. Therefore, the definitions of the terms used herein should follow contexts disclosed herein.

Combinations of blocks in the accompanying block diagrams or steps in the accompanying flowcharts can be executed by computer program instructions (execution engine), and the computer program instructions can be mounted in a processor of a general-use computer, special-use computer or other programmable data processing equipment. Thus, the instructions executed through the processor of the computer or other programmable data processing equipment generate units for performing functions described in the respective blocks of the block diagrams or the respective steps of the flowcharts.

The computer program instructions can be stored in a computer usable or readable memory oriented to a computer or other programmable data processing equipment, in order to implement functions in a specific method. Thus, the instructions stored in the computer usable or readable memory can be used to manufacture products including instruction units for performing the functions described in the respective blocks of the block diagrams or the respective steps of the flowcharts.

In addition, the computer program instructions can be mounted in the computer or other programmable data processing equipment. Therefore, instructions which generate processes by performing a series of operation steps on the computer or other programmable data processing equipment and operate the computer or other programmable data processing equipment can provide steps for executing the functions described in the respective blocks of the block diagrams and the respective steps of the flowcharts.

Further, each of the blocks or steps may indicate a part of a module, segment or code including one or more executable instructions for executing specific logical functions. In some substitutions, the functions described in the blocks or steps can be performed out of sequence. For example, two blocks or steps shown in succession may in fact be substantially executed at the same time, and the two blocks or steps may also be executed in the reverse order of the corresponding function as necessary.

Hereinafter, example embodiments of the present invention will be described in detail with reference to the accompanying drawings. However, the example embodiments may be modified in various different forms, and the scope of the present invention is not limited to the example embodiments described below. The embodiments of the present invention are provided to aid those skilled in the art in the explanation and the understanding of the present invention.

FIG. 1 a diagram illustrating the configuration of a digital dentistry device according to an embodiment of the present invention.

Referring to FIG. 1, a digital dentistry device 1 performs tooth arrangement design for dental treatments such as orthodontics, prosthetics, and dentures in actual dental practice. The tooth setup design includes a series of processes of acquiring dental image data of a patient, establishing a treatment plan by performing simulation through diagnosis and analysis using the dental image data under the control of software, and producing virtual tooth setup data in which teeth are arranged according to the established treatment plan. The tooth setup may be applied to orthodontics, prosthetics, dentures, etc.

The digital dentistry device 1 according to the embodiment may include an electronic device that can execute a tooth setup design program and a server that communicates with the electronic device through a network. Examples of the electronic device include computers, notebook computers, laptop computers, tablet personal computers (PCs), smartphones, mobile phones, and the like.

The digital dentistry device 1 confirms the dental treatment process and results in order to verify whether planned tooth movements are progressing correctly during or after dental treatment. Data comparisons used for monitoring dental treatment process and outcome through digital dentistry are proving to be a useful method for confirming whether planned tooth movements has occurred. This method may be used as a means to make comparisons before and after treatment more visible using digital data and to compare tooth movement distances using digital technology. Furthermore, the digital dentistry device 1 may confirm whether various dental treatment plans established prior to dental treatment are properly reflected in the treatment and may also verify the consistency between the treatment plan and the treatment results.

The data matching process required for data comparison is a crucial prerequisite that directly impacts the calculation of tooth movement distances. However, even with the introduction of digital dentistry technology, there is a significant reliance on the user when confirming dental treatment process and results, as the proficiency of users with the system is additionally required.

The digital dentistry device 1 according to the embodiment provides rapid matching results based on accuracy by improving two aspects: matching reference point extraction for data matching and reducing alignment processing time. The digital dentistry device 1 according to the embodiment may improve the matching accuracy of multiple dental treatment data to leverage the advantages of digital systems, reduce the waiting time for users to confirm matching results as the system presents them first, and provide consistent results, thereby lowering the reliance on user knowledge.

A configuration of the digital dentistry device 1 with the above-described features will be described with reference to FIG. 1 below.

Referring to FIG. 1, the digital dentistry device 1 according to the embodiment includes a data acquisition unit 10, a storage unit 12, a control unit 14, an input unit 16, and an output unit 18. The control unit 14 may be used interchangeably with the term "processor".

The data acquisition unit 10 acquires dental treatment data from a patient. Dental treatment data may include all types of 3D data in the form in which teeth and gum are ultimately distinguished based on 3D surface or volume data input or modified from 3D model scanners, 3D intraoral scanners, CT data conversion, and the like. The data acquisition unit 10 may obtain dental treatment data before, during, or after treatment, and may acquire dental treatment data for each treatment stage during treatment.

The control unit 14 performs data matching for checking dental treatment process and outcomes. Data matching involves overlapping at least two pieces of dental treatment data. Dental treatment data may include reference data and comparative data. The comparative data may be categorized based on treatment progress stages. For example, comparative data may include comparative data from treatment progress stage 1, comparative data from treatment progress stage 2, and so on up to comparative data from treatment progress stage N (where N is a positive integer). Thus, the control unit 14 may overlap at least two pieces of such reference data and comparative data (or multiple pieces of comparative data). For example, the control unit 14 may overlap the reference data from before treatment with comparative data 1 from treatment progress stage 1 and also overlap the reference data from before treatment with comparative data from treatment progress stage 2. Additionally, the control unit 14 may overlap the reference data from before treatment, comparative data 1 from treatment progress stage 1, and comparative data 2 from treatment progress stage 2.

The control unit 14, when receiving at least two pieces of dental treatment data through the data acquisition unit 10, may preferably automatically match the at least two pieces of dental treatment data and generate a matching result. Here, the matching result refers to new dental treatment data created by matching the at least two pieces of dental treatment data. The matching result may be displayed through the output unit 18.

For data matching, it is essential to have at least one matching reference point as the matching basis. The control unit 14 may automatically extract matching reference points from each dental treatment data even without user input, using computer calculations. To this end, the control unit 14 may perform operations of separating the gum and individual teeth in each data, obtaining landmarks (i.e. feature points) on the individual teeth, and extracting matching reference points from the individual tooth landmarks.

To enhance the accuracy of data matching result, the control unit 14 may divide the entire tooth area within the data into a plurality of regions and extract matching reference points from among the landmarks on individual teeth within the divided regions.

In one embodiment, the matching reference points may be determined based on tooth movement information. The control unit 14 uses the tooth movement information to confirm the presence of fixed teeth within the regions. The tooth movement information includes information regarding the movement status and the movement amount of individual teeth planned during dental treatment plan creation, which may be obtained when acquiring each dental treatment data.

In this case, if there is at least one region where the fixed teeth are located, i.e., a fixed region, the control unit 14 extracts the matching reference points centered around the fixed teeth. If it is determined that all teeth have moved based on tooth movement information, the control unit 14 extracts the matching reference points centered around the tooth with the least tooth movement. The plurality of regions may include, for example, regions composed of the anterior teeth, the left posterior teeth, and the right posterior teeth, but are not limited thereto.

The landmarks for the individual teeth may include at least one of occlusal-direction landmarks and adjacent-direction landmarks for each individual tooth, but are not limited thereto. The occlusal-direction landmark is an occlusal point between an upper target tooth of the patient's maxilla and the corresponding lower tooth of the mandible, while the adjacent-direction landmark is a point of contact between a target tooth and an adjacent tooth.

Before performing matching, the control unit 14 may compare the size, area, position, and the like of figures formed by connecting the matching reference points for each data, and calculate a deviation between the figures. In this case, if the deviation is within a predefined range, the control unit 14 uses the extracted matching reference points to perform data matching. In contrast, if the deviation between the figures exceeds the predetermined range, the control unit

14 may modify the extracted matching reference points and use the modified matching reference points to perform data matching. As a result, the digital dentistry device 1 determines the matching result variance before performing the matching and provides it to the user, thus reducing the calculation time required for matching and matching result comparison.

The control unit 14, when a matching reference point deviation occurs, may display the deviation through the output unit 18 and may also display a user interface for user modifications through the output unit 18. Consequently, the matching reference point positions may be modified by user interaction with the user interface.

The control unit 14 according to the embodiment may acquire multiple landmarks associated with individual teeth from at least two pieces of scan data, and then determine at least three of the multiple landmarks as matching reference points based on the area of a figure created using at least some of the multiple landmarks as vertices. Then, the control unit 14 may match at least two pieces of scan data using these determined at least three matching reference points.

The control unit 14 according to the embodiment may obtain at least two pieces of scan data that can be divided into a first region corresponding to the anterior teeth, a second region corresponding to the left posterior teeth, and a third region corresponding to the right posterior teeth. Then, the control unit 14 may designate each of the first to third regions as either a fixed or moving region based on tooth movement information. In addition, depending on the number of fixed regions, different conditions may be applied to determine at least three matching reference points in at least one of the first to third regions. Subsequently, the control unit 14 may match at least two pieces of scan data using the determined matching reference points.

The storage unit 12 stores various data, including information necessary for the operation of the digital dentistry device 1 and data generated during operation. The storage unit 12 may provide the control unit 14 with the data required for data processing.

The output unit 18 displays a screen according to the operation performed by the control unit 14. For example, the output unit 18 may display dental treatment data, matching processes, matching results, and the like on the screen. Before data matching, the output unit 18 may display deviation between the matching reference points in a distinguished manner using identifiable visual information. Additionally, after data matching, the output unit 18 may display the tooth movement deviation or matching deviation between data in a distinguished manner using identifiable visual information.

The input unit 16 receives a user manipulation signal. For example, the input unit 16 may receive a manipulation signal for user modification such as navigation or rotation on the user interface displayed on the screen through the output unit 18.

Figure 2:
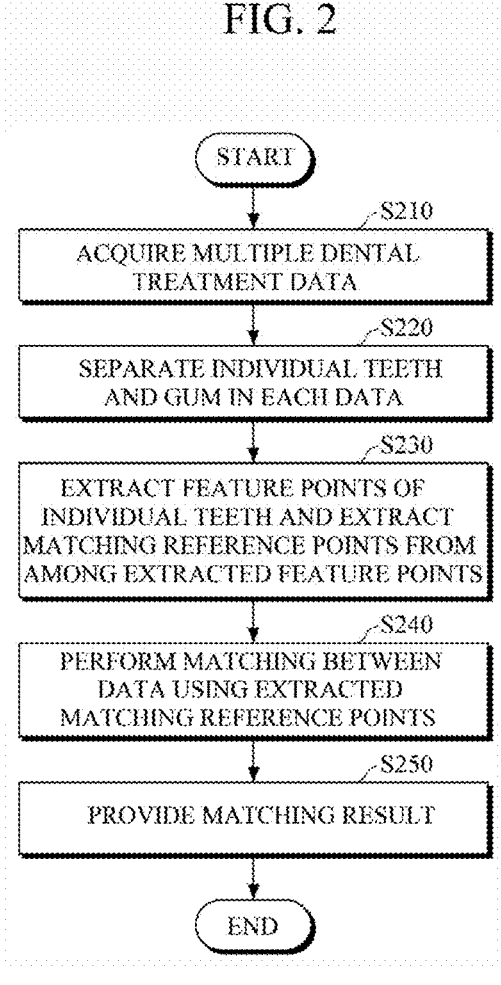
FIG. 2 is a flowchart illustrating a dental treatment data matching method according to an embodiment of the present invention.

FIG. 2 is a flowchart illustrating a dental treatment data matching method according to an embodiment of the present invention.

Referring to FIGS. 1 and 2, in operation S210, the digital dentistry device 1 acquires at least two pieces of dental treatment data to be matched. For example, dental treatment data may include various types of 3D data, preferably 3D intraoral scan data. However, pieces of dental treatment data to be matched must be of the same type. For example, if one piece of dental treatment data is 3D intraoral scan data, the other data to be matched with it must also be 3D intraoral scan data.

The digital dentistry device 1 may acquire dental treatment data before or after the treatment. In addition, the digital dentistry device 1 may also acquire dental treatment data during the course of dental treatment. Pieces of dental treatment data acquired during the treatment may be distinguished from each other based on the treatment stage. Matching targets may include previously planned data and current data during treatment, or current data during treatment and data planned for future treatment, or the data being acquired during treatment.

Then, in operation S220, the digital dentistry device 1 separates individual teeth and gum for each acquired data. The control unit 14 may achieve data consistency by applying the same method to each dental treatment data during the separation of individual teeth and gum, thus preventing errors that can occur during separation. The control unit 14 may distinguish individual teeth and gum using image boundary detection. Separation methods may include, for example, a method of assuming pixel values in image data as a two-dimensional terrain and dividing areas by filling water in pixels with values lower than a reference value and creating dams in areas where water overflows, a method of separating areas based on user selection, and the like.

Subsequently, in operation S230, the digital dentistry device 1 extracts landmarks of the individual teeth from the data associated with the separated individual teeth and gum and obtains the matching reference points from among these landmarks.

The landmarks of the individual teeth may include at least one of occlusal-direction landmarks and adjacent-direction landmarks for each individual tooth. The digital dentistry device 1 may divide the tooth area into a plurality of regions for each data and confirm the presence of a fixed tooth in each region by checking the tooth movement information of individual teeth within the divided regions.

In one embodiment, when there is at least one fixed area where a fixed tooth exists, the control unit 14 may obtain the matching reference points centered around the fixed tooth. For example, if there is at least one fixed area where a fixed tooth exists, the control unit 14 may calculate the area of a figure formed by connecting at least three of the landmarks of the fixed tooth, and determine at least three points that form the figure with the largest area as matching reference points.

In one embodiment, when there is no fixed area (i.e., when all teeth are moving without a fixed tooth), the control unit 14 may extract matching reference points centered around the tooth with the least tooth movement. For example, if at least one fixed area does not exist, the control unit 14 extracts the three teeth with the least tooth movement based on the tooth movement information. The control unit 14 checks the area of a figure formed by connecting at least three points from the characteristic points of the extracted moving teeth and determines at least three points that form the shape with the largest area as matching reference points.

In one embodiment, the control unit 14 may obtain matching reference points from individual teeth using a pre-trained artificial intelligence model, for example, a neural network model. The artificial intelligence model is supervised trained on training data labeled with ground truth information, and it may be implemented as a neural network model. The neural network model may include an artificial neural network (ANN), a convolutional neural network (CNN), a recurrent neural network (RNN), and other neural network structures. In one embodiment, the training data includes dental treatment data with annotated landmarks and reference points associated with individual teeth, preferably scan data. The artificial intelligence model trained based on the training data, when dental treatment data are provided to an input layer, generates landmarks and matching reference points associated with individual teeth as outputs on the input dental treatment data. Here, the landmarks correspond to specific anatomical features (e.g., occlusal points, adjacent points), and the matching reference points are at least three of these landmarks that correspond to vertices of the figure with the largest area.

In operation S240, the control unit 14 matches at least two pieces of dental treatment data based on one or more, preferably at least two, and more preferably at least three matching reference points.

The control unit 14, preferably before performing matching, may calculate the deviation between the figures formed by connecting the matching reference points of each data. Based on the deviation, the control unit 14 may match the data using the matching reference points or modified matching reference points. For example, if the deviation is within a predetermined range, the extracted matching reference points are used for matching the data. In another example, if the deviation between the figures exceeds the predetermined range, modified matching reference points are used for matching data. Here, the modified matching reference points are those that have been modified from the originally extracted matching reference points. The matching reference points may be modified manually by the user, or modified by the digital dentistry device 1. When the digital dentistry device 1 performs the modifications, it may calculate, for example, the deviations individually for each matching reference point and modify the matching reference point positions. Accordingly, the movement of equal deviation may be taken into account in the correction of the matching reference point.

The aforementioned embodiment describes an example of pre-calculation of a deviation between the figures by comparing the areas of the figures generated when connecting the matching reference points, but it is also possible to pre-calculate a deviation between the figures by comparing their positions or sizes. In this case, the digital dentistry device 1 may display the deviation between the figures of each data on the screen as a numerical value, and may display the numerical deviation on the screen in a distinguished manner using identifiable visual information.

In operation S250, after data matching, the digital dentistry device 1 displays the data matching results on the screen. Additionally, after data matching, the digital dentistry device 1 may display the tooth movement deviation or matching deviation between the data in a distinguished manner using identifiable visual information. For example, the tooth movement deviation or matching deviation between data may be displayed using a color map.

Figure 3:
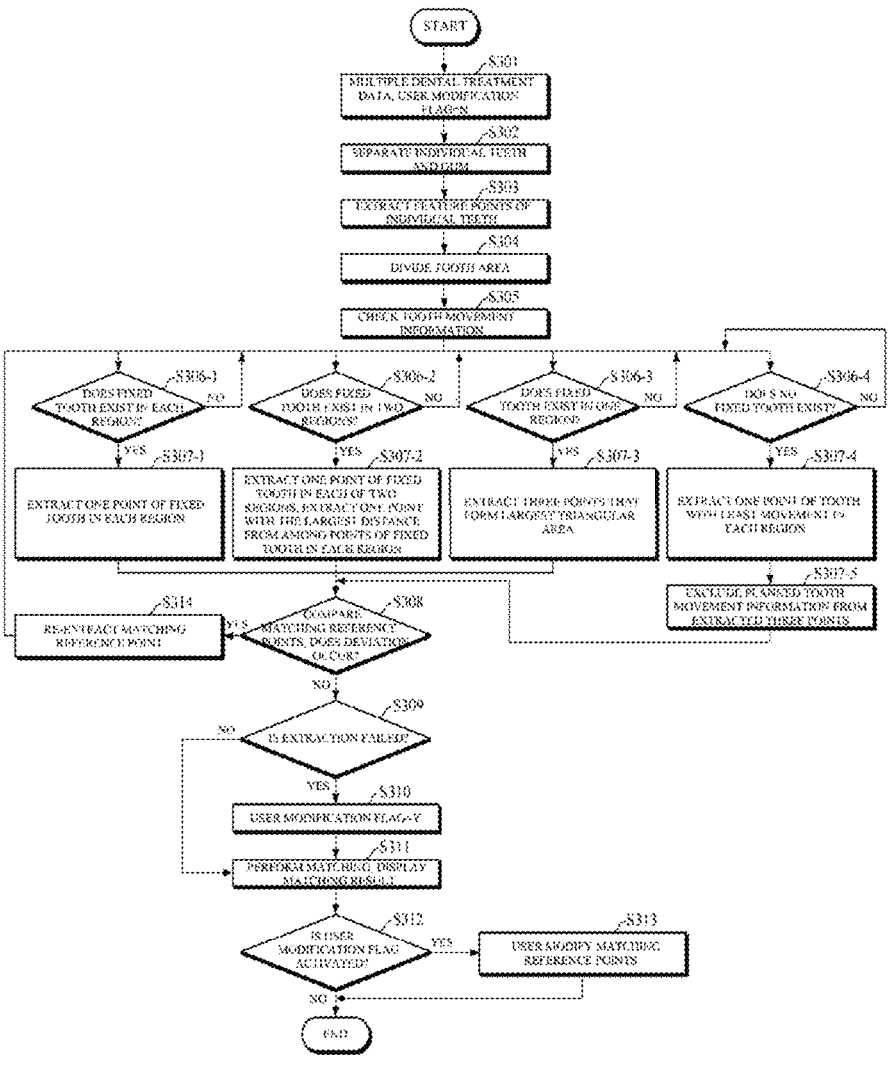
FIG. 3 is a detailed flowchart illustrating a dental treatment data matching method according to an embodiment of the present invention.

FIG. 3 is a detailed flowchart illustrating a dental treatment data matching method according to an embodiment of the present invention.

Referring to FIGS. 1 and 3, in operation S301, the digital dentistry device 1 acquires at least two pieces of dental treatment data to be matched and initializes a user modification flag (Flag=N).

Subsequently, in operation S302, the digital dentistry device 1 separates the individual teeth and gum for each dental treatment data to be matched.

Next, in operation S303, the digital dentistry device 1 extracts landmarks of each tooth from the separated individual teeth in each dental treatment data. The landmarks may be occlusal-direction landmarks and adjacent-direction landmarks. The control unit 14 may achieve data consistency by applying the same method to each dental treatment data during the extraction of landmarks, thus preventing errors that may occur during extraction. The occlusal-direction landmarks of the respective teeth are different.

Next, in operation S304, the digital dentistry device 1 divides a tooth area of each data into a plurality of regions. For example, the tooth area may be divided into an anterior teeth region, a left posterior teeth area, and a right posterior teeth area 830 (see FIG. 8).

Next, in operation S305, the digital dentistry device 1 acquires tooth movement information contained in each dental treatment data when obtaining each dental treatment data and checks the tooth movement information. The control unit 14 may classify individual teeth into moving teeth and fixed teeth based on the tooth movement information and may also distinguish the individual movement amounts of moving teeth. The control unit 14 may store the tooth movement information as 'the movement amounts of the landmarks of each individual tooth.' It should be noted that the tooth movement information may not have a clear reference and may change depending on the reference. In contrast, the 'movement amounts of the landmarks of each individual tooth' are movement information based on the landmarks for each individual tooth, so the reference may be clearer.

Then, in operations S306-1, S306-2, S306-3, and S306-4, the digital dentistry device 1 determines whether there is a fixed tooth based on the tooth movement information. In this case, possible scenarios include all three regions having a fixed tooth, two of the three regions having a fixed tooth, one of the three regions having a fixed tooth, and all three regions having moving teeth without a fixed tooth.

In operation S306-1, if it is determined that there is a fixed tooth in all three regions, the digital dentistry device 1 in operation S307-1 extracts one of the landmarks of the fixed tooth from each of the three regions with the fixed tooth as matching reference points, resulting in a total of three matching reference points.

In contrast, in operation S306-2, if it is determined that there is a fixed tooth in two of the anterior teeth, left posterior teeth, and right posterior teeth regions, the digital dentistry device 1 in operation S307-2 extracts one of the landmarks of the fixed tooth from each of the two regions with the fixed tooth as matching reference points. Additionally, the digital dentistry device 1 further extracts one of the landmarks of the fixed teeth in the two regions having a largest distance from the fixed teeth, resulting in a total of three matching reference points. For example, since there are a plurality of landmarks for each fixed tooth, the digital dentistry device 1 extracts one landmark from the landmarks in a first region with a first fixed tooth and one landmark from the second region with a second fixed tooth, and then it determines a new landmark in each region with the largest distance between them. From these newly extracted landmarks, the digital dentistry device 1 ultimately extracts one of the landmarks with the farthest distance from the previously extracted landmark as the new fixed tooth landmark.

On the other hand, in operation S306-3, if it is determined that there is only one region with a fixed tooth among the anterior teeth, left posterior teeth, and right posterior teeth regions, the digital dentistry device 1 in operation S307-3 extracts three landmarks from the landmarks of the fixed tooth in the single region, which can form the largest triangle area, as the matching reference points, resulting in a total of three matching reference points.

In contrast, in operation S306-4, if it is determined that there are no fixed teeth in any of the anterior teeth, left posterior teeth, and right posterior teeth regions, the digital dentistry device 1 in operation S307-4 extracts the tooth with the least tooth movement (the least moving tooth) from each region, and extracts one landmark for each of the three least moving teeth that can form the largest triangle area as the matching reference point, resulting in a total of three matching reference points.

In operation S307-5, the digital dentistry device 1 excludes the planned tooth movement information from the extracted three matching reference points. In other words, since there are no fixed teeth, errors may occur during the matching reference point extraction. For example, when planned first movement information (e.g., planned total movement amount of three moving points: 1 mm) is different from second tooth movement information during the current matching reference point extraction (e.g., the total movement amount of three reference points is greater or less than 1 mm), errors may occur. To minimize such errors, the digital dentistry device 1 may calculate the difference between the second tooth movement information and the first tooth movement information through subtraction, and determine whether an error has occurred based on the difference.

Subsequently, in operation S308, the digital dentistry device 1 connects three points of each dental treatment data to create a triangle, and determines whether a matching reference point deviation occurs by comparing at least one of the area, position, or size of the created triangles of the data.

If the matching reference point deviation occurs, the digital dentistry device 1 re-extracts the matching reference points in operation S314.

In contrast, when no matching reference point deviation occurs, the digital dentistry device 1 in operation S309 determines whether there are additional matching reference points to extract.

In case of extraction failure (i.e., when there are no more landmarks to extract as matching reference points), the digital dentistry device 1 in operation S310 determines a reference point representing the final deviation value as the final reference point and activates the user modification flag (Flag=Y).

Subsequently, in operation S311, the digital dentistry device 1 performs matching of the dental treatment data using the three matching reference points and displays the matching result on the screen.

Next, in operation S312, the digital dentistry device 1 may check whether the user modification flag is activated. If the user modification flag is activated, the digital dentistry device 1 in operation S313 may display the deviation of the matching reference points used during matching and modify the matching reference points through user manipulation. On the other hand, if the user modification flag is not activated, the digital dentistry device 1 concludes the matching.

Figure 4:
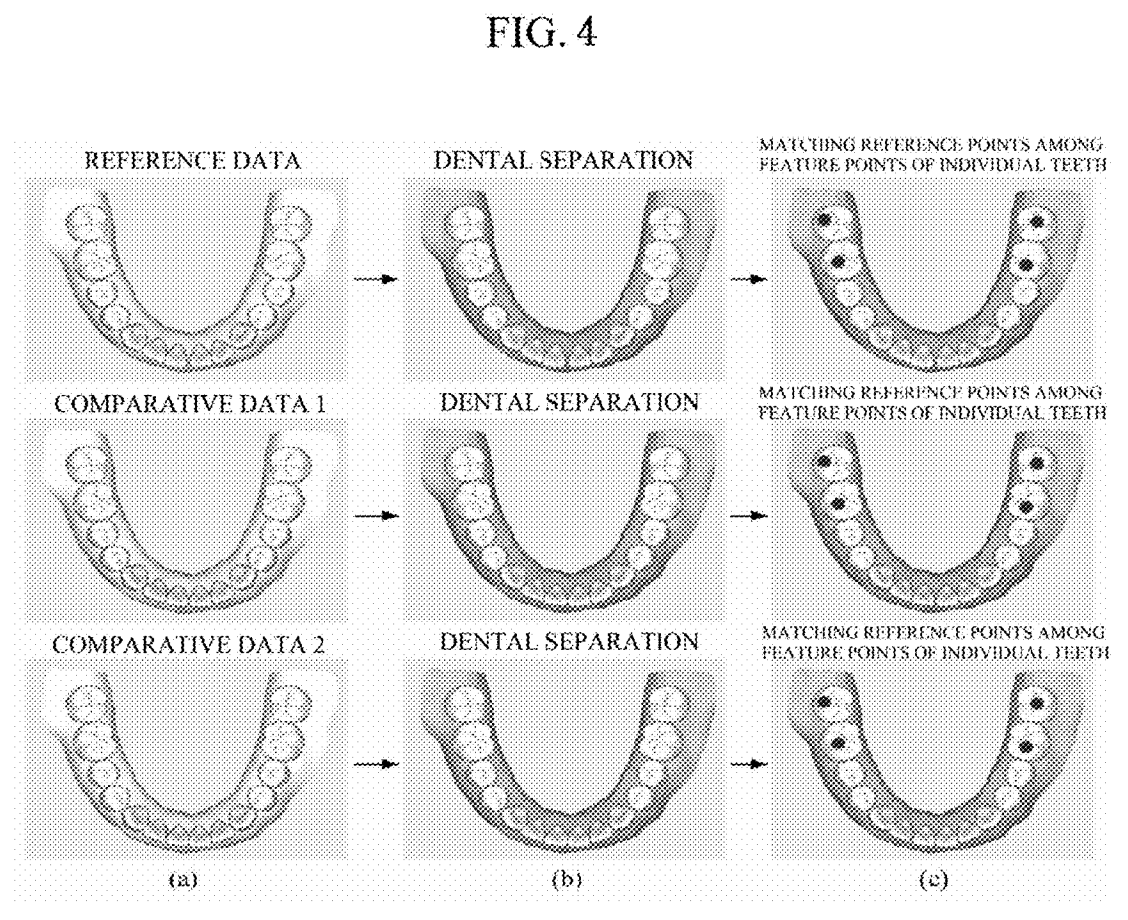

FIG. 4 illustrates screens for extracting matching reference points for matching between pieces of data according to an embodiment of the present invention.

Referring to FIGS. 1 and 4, the digital dentistry device 1 acquires at least two pieces of dental treatment data to be matched, as shown in (a) in FIG. 4. For example, as illustrated in FIG. 4, the digital dentistry device 1 acquires reference data, comparative data 1, and comparative data 2. The reference data may be 3D scan data before treatment, comparative data 1 may be 3D scan data at a first stage of treatment, and comparative data 2 may be 3D scan data at a second stage of treatment. In the example shown in FIG. 4, it is observed that the gap between the central incisors narrows and they become closer as the treatment progresses as shown in the reference data and comparative data 1 and 2.

Next, the digital dentistry device 1 separates individual teeth and gum for each acquired data, as shown in (b) of FIG. 4.

Subsequently, the digital dentistry device 1, as shown in (c) of FIG. 4, extracts landmarks of the individual teeth for each separated data and extracts matching reference points from the extracted landmarks. In this case, the digital dentistry device 1 may extract the matching reference points from the landmarks of fixed teeth or moving teeth using tooth movement information.

Figure 5:
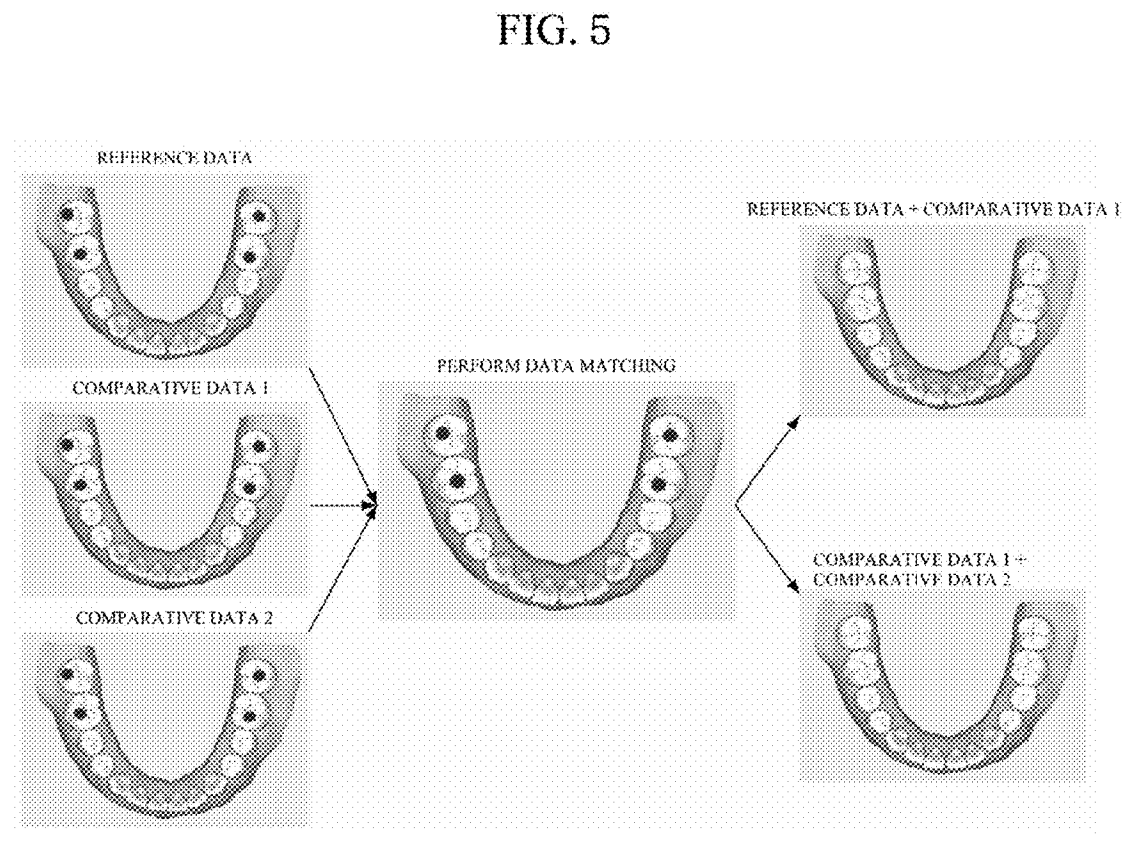

FIG. 5 illustrates screens for matching between pieces of data using matching reference points extracted according to an embodiment of the present invention.

Referring to FIGS. 1, 4, and 5, the digital dentistry device 1 may perform data matching by overlapping data to be matched (e.g., reference data, comparative data 1, and comparative data 2). In this case, the digital dentistry device 1 may perform data matching by overlapping the reference data with comparative data 1, comparative data 1 with comparative data 2, or the reference data with comparative data 2.

Figure 6:
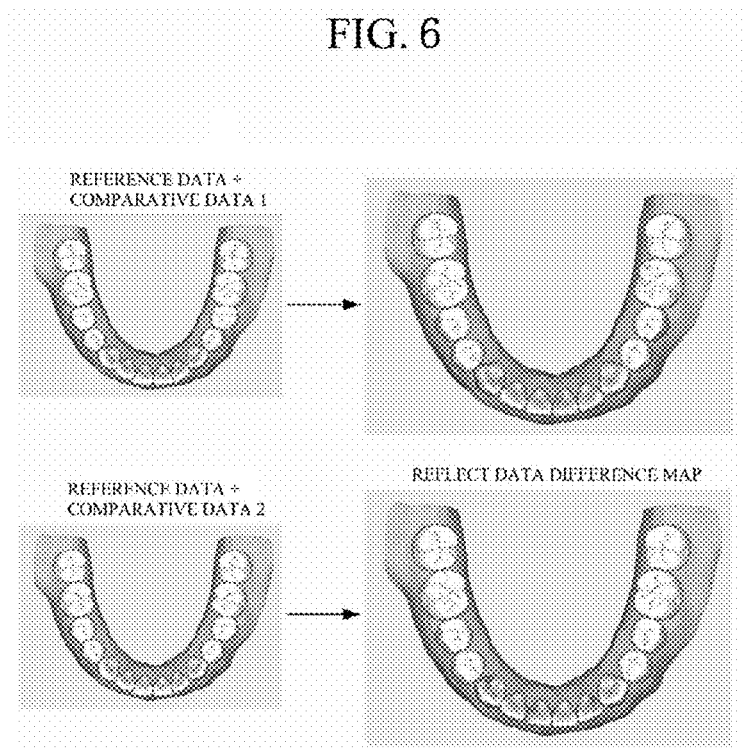
FIG. 6 illustrates matching result screens according to an embodiment of the present invention.

FIG. 6 illustrates matching result screens according to an embodiment of the present invention.

Referring to FIGS. 1 and 6, the digital dentistry device 1 displays a matching result after performing matching between data. In this case, the digital dentistry device 1 may display the tooth movement deviation or matching deviation between the data in a distinguished manner using identifiable visual information. For example, as shown in FIG. 6, the digital dentistry device 1 may display the tooth movement deviation or matching deviation that occurs during the matching between the reference data and comparative data 1 using a color map. Similarly, the digital dentistry device 1 may display the tooth movement deviation or matching deviation that occurs during the matching between comparative data 1 and comparative data 2 using a color map. The user may visually check the matching deviations by looking at the colors on the color map.

Figure 7:
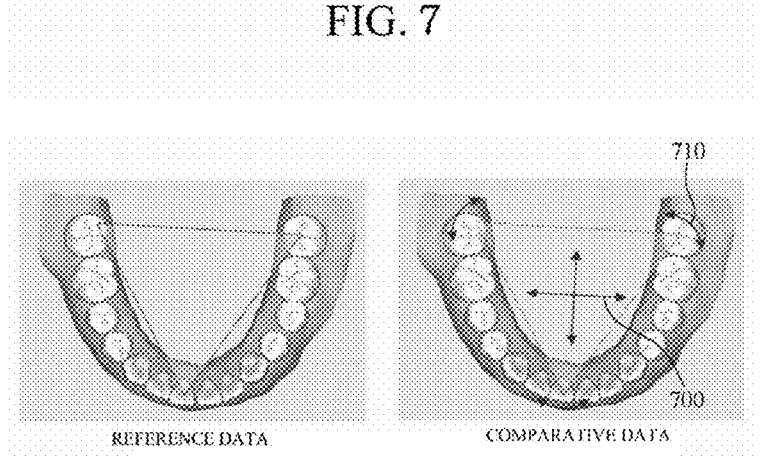
FIG. 7 illustrates screens for a user to modify matching reference points by a user when a deviation occurs between matching reference points according to an embodiment of the present invention.

FIG. 7 illustrates screens for a user to modify matching reference points when a deviation occurs between the matching reference points according to an embodiment of the present invention.

Referring to FIG. 1 and FIG. 7, when a deviation occur between the matching reference points of dental treatment data to be matched, the digital dentistry device 1 displays the matching reference point positions before data matching, allowing the user to modify them. This approach involves allowing the user to modify the matching reference points extracted by the digital dentistry device 1, which helps reduce the calculation time required for data matching and result comparison. For example, as shown in FIG. 7, while keeping the matching reference points of the comparative data fixed (e.g., in a triangular shape), the digital dentistry device 1 reflects and displays the matching reference points of the reference data (e.g., in a triangular shape) onto the comparative data. In this case, the digital dentistry device 1 may also display a first user interface 700 on the screen for modifying the matching reference points of the reference data displayed on the comparative data, allowing the user to modify the overall position of the matching reference points by manipulating the first user interface 700. In another example, instead of modifying the overall position of the matching reference points, the digital dentistry device 1 may display a second user interface 710 along with the comparative data on the screen, allowing the user to individually modify the positions of individual matching reference points by manipulating the second user interface 710.

When the user modifies the matching reference points, the digital dentistry device 1 may display the results of matching reference point deviations due to the modifications, in numerical values or visual information, supporting the user in confirming the need for additional modification.

As another example, the user may initialize the matching reference points that the digital dentistry device 1 has extracted, and extract new matching reference points. This approach also involves enabling the user to first check the deviation between matching reference points and modify the relevant matching reference points before data matching, thereby reducing the calculation time required for data matching and result comparison.

Figure 8:
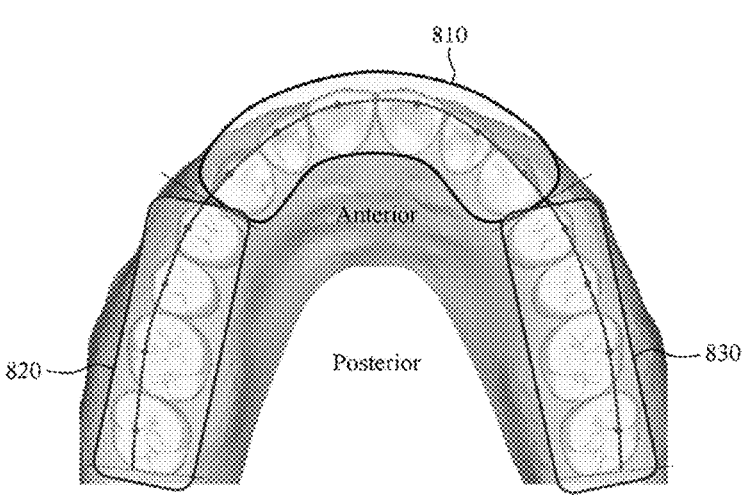
FIG. 8 illustrates a screen for dividing a tooth area for extracting matching reference points according to an embodiment of the present invention.

FIG. 8 illustrates a screen for dividing a tooth area for extracting matching reference points according to an embodiment of the present invention.

Referring to FIGS. 1 and 8, the digital dentistry device 1 may divide a tooth area into a plurality of regions to extract matching reference points. For example, the tooth area may be divided into an anterior teeth region 810, a left posterior teeth area 820, and a right posterior teeth area 830, as shown in FIG. 8.

Heretofore, the present invention has been described by focusing on the exemplary embodiments. It can be understood by those skilled in the art to which the present invention pertains that the present invention can be implemented in modified forms without departing from the essential feature of the present invention. Therefore, the disclosed embodiments should be considered as illustrative rather than determinative. The scope of the present invention is defined by the appended claims rather than by the foregoing description, and all differences within the scope of equivalents thereof should be construed as being included in the present invention.

The invention claimed is:

1. A dental treatment data matching method comprising:
   acquiring at least two pieces of dental treatment data to be matched;
   separating individual teeth and gum in each of the acquired data;
   extracting feature points of the individual teeth for each of the separated data;
   extracting matching reference points based on tooth movement from among the extracted feature points;
   performing matching between the pieces of data using the extracted matching reference points; and
   displaying a matching result,
   wherein the extracting of the matching reference points comprises:
   dividing a tooth area into a plurality of regions in each data;
   determining whether a fixed tooth exists in each divided region by checking tooth movement information of the individual teeth in each divided region; and
   when there is at least one fixed region where a fixed tooth exists, extracting the matching reference points centered around the fixed tooth; or
   when all teeth move without a fixed tooth, extracting the matching reference points centered around a tooth with the least tooth movement, and
   wherein in the extracting of the matching reference points centered around the fixed tooth, when there is at least one fixed region where a fixed tooth exists, three or more feature points that form the largest area when connected are extracted from among feature points of the fixed tooth as the matching reference points.

2. The dental treatment data matching method of claim 1, wherein in the extracting of the feature points of the individual teeth, at least one of occlusal-direction feature points or adjacent-direction feature points is extracted for each of the individual teeth.

3. The dental treatment data matching method of claim 1, wherein in the extracting of the matching reference points centered around the fixed tooth, when there is not at least one fixed region where a fixed tooth exists, a predetermined number of individual teeth with the least tooth movement are extracted, followed by extracting three or more feature points that form the largest area when connected from among feature points of the extracted individual teeth as the matching reference points.

4. A dental treatment data matching method comprising:
acquiring at least two pieces of dental treatment data to be matched;
separating individual teeth and gum in each of the acquired data;
extracting feature points of the individual teeth for each of the separated data;
extracting matching reference points based on tooth movement from among the extracted feature points;
performing matching between the pieces of data using the extracted matching reference points; and
displaying a matching result,
wherein, before matching, forming figures by connecting the matching reference points extracted for each data and pre-calculating a deviation between the figures by comparing at least one of an area, position, or size of the formed figures of each data, and
wherein the performing of matching between the pieces of data comprises,
when the calculated deviation between the figures is within a predetermined value range, performing matching between the pieces of data using the extracted matching reference points, or
when the calculated deviation between the figures is outside the predetermined value range, modifying the extracted matching reference points, followed by performing matching between the pieces of data using the modified matching reference points.

5. The dental treatment data matching method of claim 4, further comprising at least one of:
displaying the deviation between the figures of each data as a numerical value on a screen; or
displaying a numerical deviation in a distinguished manner using identifiable visual information on the screen.

6. The dental treatment data matching method of claim 1, further comprising:
in order to modify the extracted matching reference points, while keeping matching reference points of comparative data fixed, reflecting and displaying reference matching points of reference data onto the comparative data, and providing a user interface together on a screen for modifying the reference matching points of the reference data displayed on the comparative data; and
modifying at least one of the matching reference points by user interaction with the user interface.

7. The dental treatment data matching method of claim 1, wherein in the extracting of the feature points of individual teeth for each of the separated data and the extracting of the matching reference points from among the extracted feature points, artificial intelligence-based machine learning on training data including previously accumulated multiple dental treatment data is performed and feature points and matching reference points are extracted from newly input dental treatment data using the training data.

8. The dental treatment data matching method of claim 1, wherein in the displaying of the matching result, after performing data matching, a tooth movement deviation or matching deviation between the data is displayed in a distinguished manner using identifiable visual information.

9. A digital dentistry device comprising:
a data acquisition unit configured to acquire at least two pieces of dental treatment data to be matched;
a control unit configured to separate individual teeth and gum in each of the acquired data, extract feature points of the individual teeth for each of the separated data, extract matching reference points based on tooth movement from among the extracted feature points, and perform matching between the pieces of data using the extracted matching reference points; and
an output unit configured to display a screen according to an operation of the control unit and display a matching result,
wherein the control unit, before matching, forms figures by connecting the matching reference points extracted for each data, pre-calculates a deviation between the figures by comparing at least one of an area, position, or size of the formed figures of each data, and, when the calculated deviation between the figures is within a predetermined value range, performs matching between the pieces of data using the extracted matching reference points, or when the calculated deviation between the figures is outside the predetermined value range, modifies the extracted matching reference points, followed by performing matching between the pieces of data using the modified matching reference points.

10. The digital dentistry device of claim 9, wherein the control unit divides a tooth area into a plurality of regions in each data, determines whether a fixed tooth exists in each divided region by checking tooth movement information of the individual teeth in each divided region, and when there is at least one fixed region where the fixed tooth exists, extracts the matching reference points centered around the fixed tooth, or when all teeth move without a fixed tooth, extracts the matching reference points centered around a tooth with the least tooth movement.

* * * * *